United States Patent [19]

Green

[11] Patent Number: 4,915,100
[45] Date of Patent: * Apr. 10, 1990

[54] SURGICAL STAPLER APPARATUS WITH TISSUE SHIELD

[75] Inventor: David T. Green, Westport, Conn.

[73] Assignee: United States Surgical Corporation, Norwalk, Conn.

[*] Notice: The portion of the term of this patent subsequent to Nov. 21, 2006 has been disclaimed.

[21] Appl. No.: 286,506

[22] Filed: Dec. 19, 1988

[51] Int. Cl.$^4$ ............................................. A61B 17/04
[52] U.S. Cl. .................................... 227/176; 227/178; 227/180
[58] Field of Search ........ 128/334 R; 227/19, DIG. 1

[56] References Cited

U.S. PATENT DOCUMENTS 4,354,628 10/1982 Green ................................... 227/19
4,665,916 5/1987 Green .............................. 128/334 R Primary Examiner—Edward M. Coven
Assistant Examiner—Gary Jackson
Attorney, Agent, or Firm—Peter G. Dilworth; Rocco S. Barrese; Thomas R. Bremer

[57] ABSTRACT

An improved surgical stapler for simultaneously applying a plurality of surgical fasteners to body tissue incorporating a flexible resilient U-shaped shield mounted to and around the end of the anvil assembly for separating extraneous body tissue from tissue to be fastened, and for preventing extraneous body tissue from entering the gap between the anvil assembly and fastener holder.

20 Claims, 4 Drawing Sheets

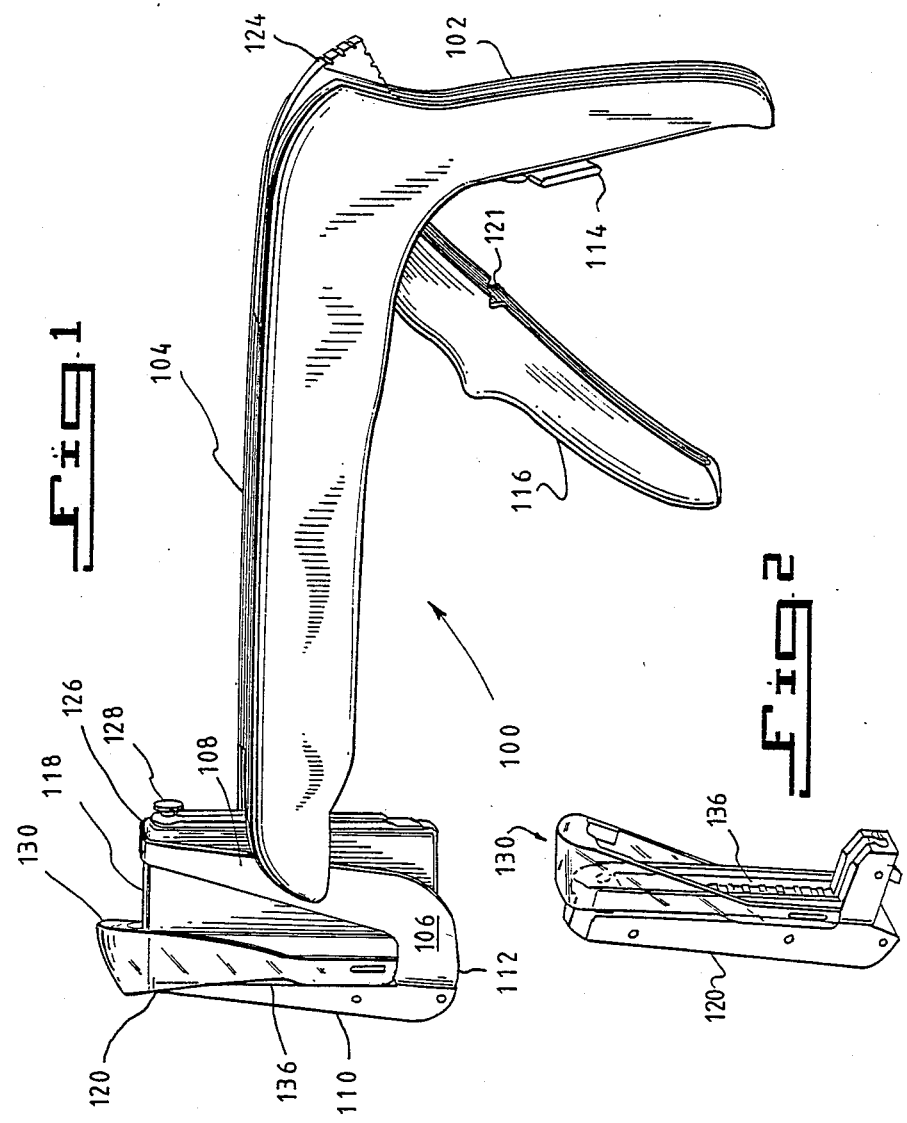

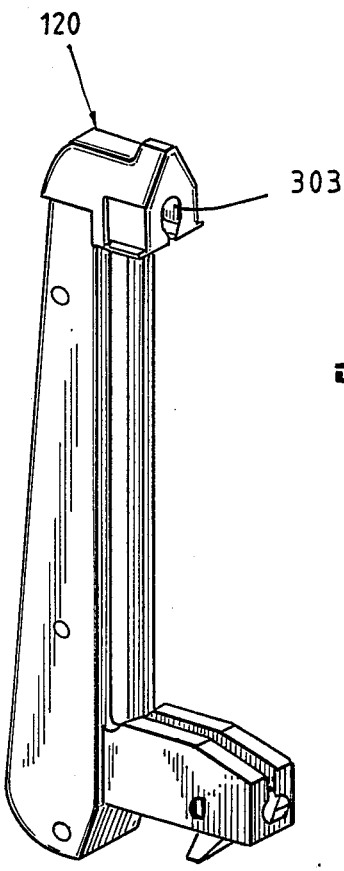
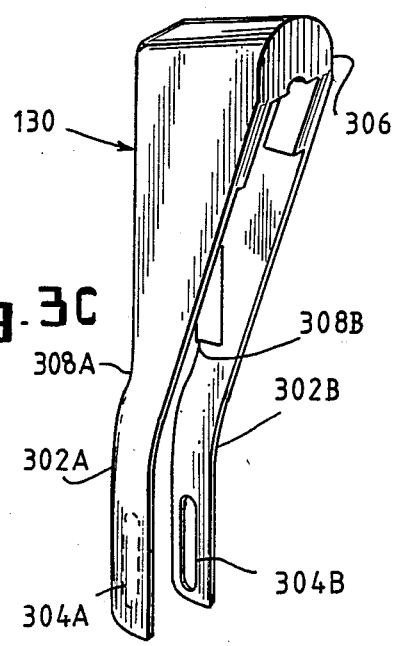
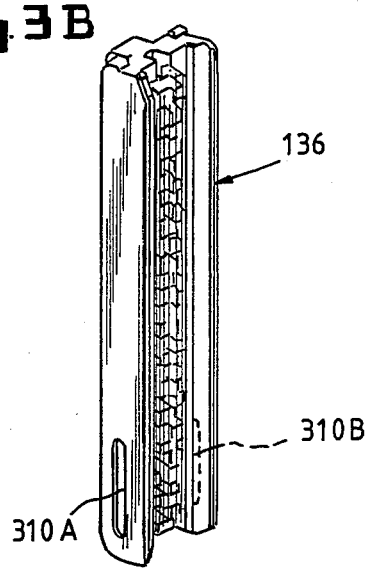

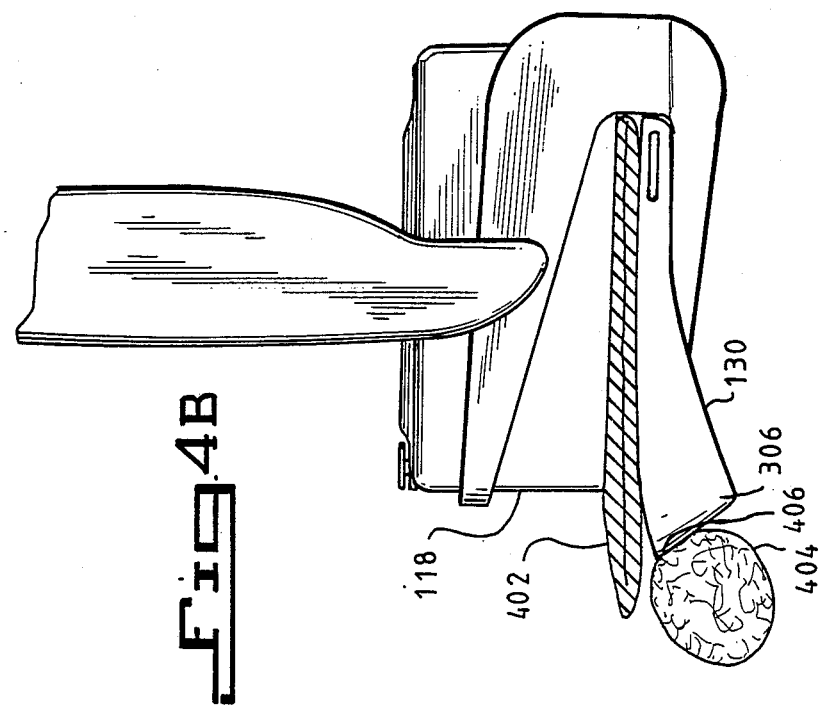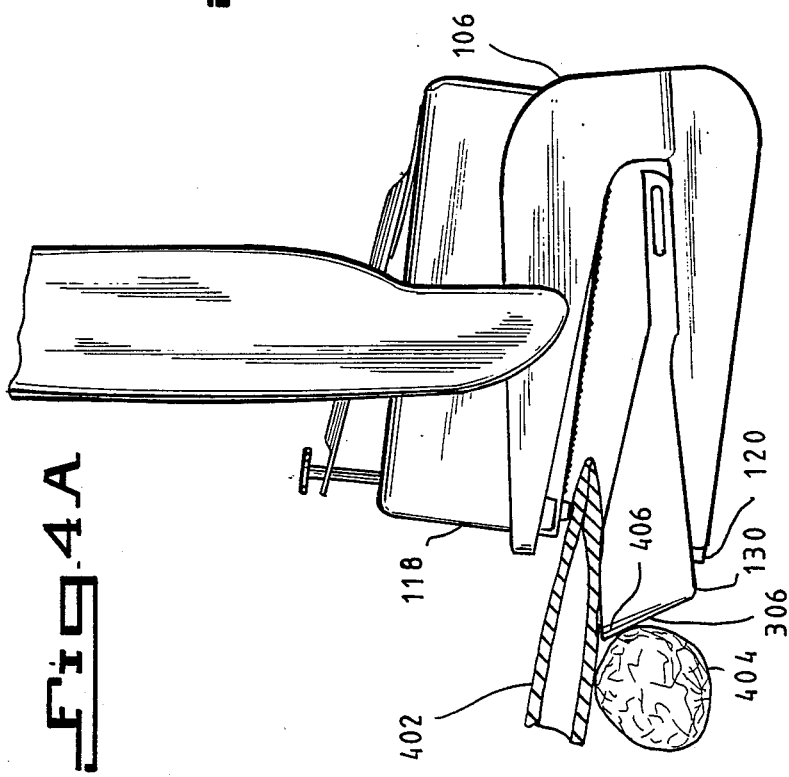

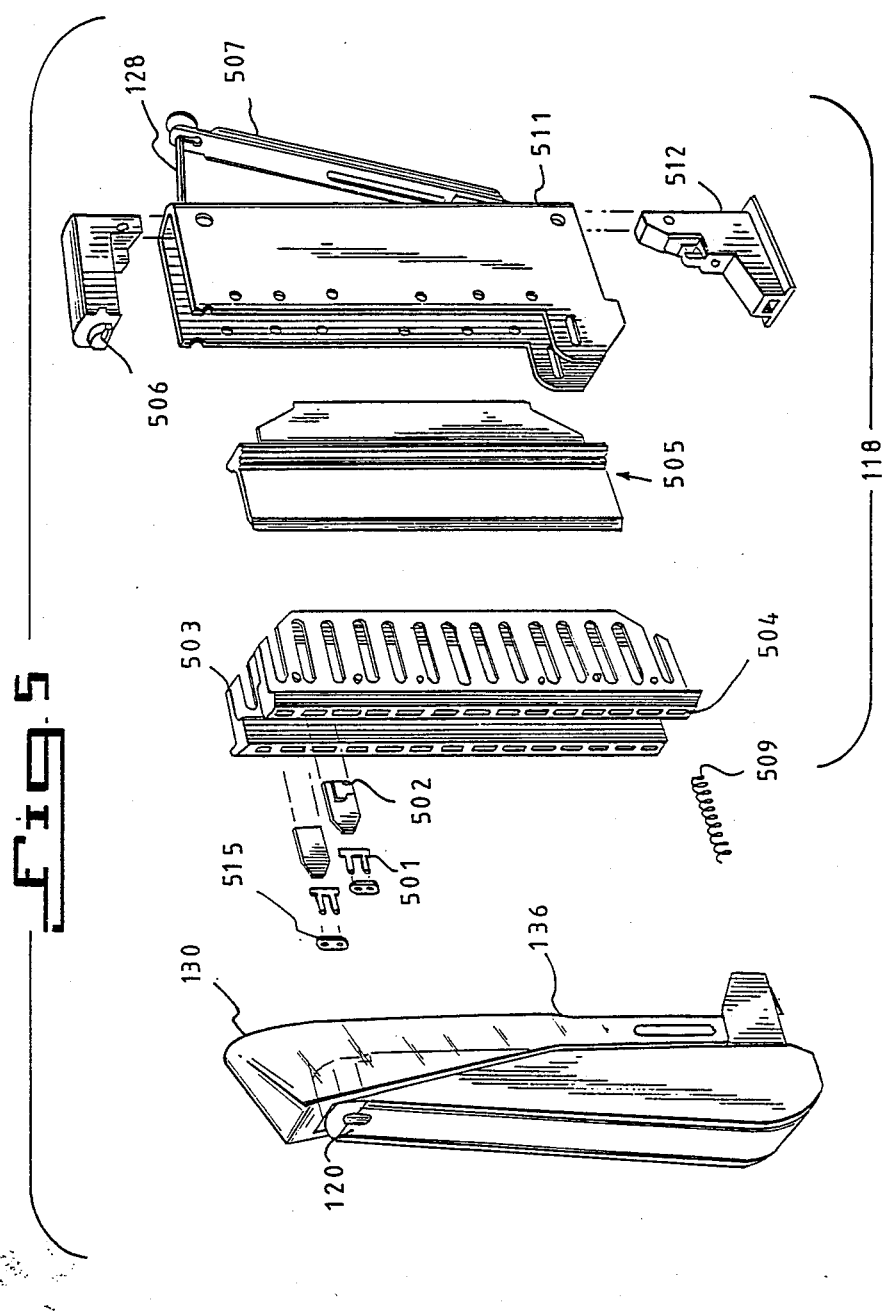

SURGICAL STAPLER APPARATUS WITH TISSUE SHIELD

BACKGROUND OF THE INVENTION

1. Field Of The Invention

This invention relates to surgical stapling apparatus, and more particularly to a surgical stapling apparatus incorporating a safety shield for protecting extraneous body tissue from the operation of the stapler.

2. Description Of Related Art

Surgical stapling apparatus in which a plurality of surgical fasteners are applied substantially simultaneously to produce an array or surgical fasteners are known. Typically these apparatus include a fastener holder disposed on one side of the tissue to be fastened, an anvil assembly parallel to the fastener holder on the other side of the tissue to be fastened, means for linearly translating the fastener holder and the anvil assembly toward one another so that the tissue is clamped between them, and means for driving the fasteners from the fastener holder so that the ends of the fasteners pass through the tissue and form finished fasteners as they make contact with the anvil assembly, thereby producing an array of finished fasteners in the tissue. The term "fasteners" is used herein as a generic term for metal surgical staples, the staple-shaped portion of one part or two part resinous surgical fasteners, and their equivalents. Similarly, the term "anvil assembly" is used herein as a generic term to include the anvil used to clinch metal surgical staples, the retainer holder and retainer member of two-part resinous surgical fasteners, and the equivalent of these elements.

In common use are devices such as those disclosed in U.S. Pat. Nos. 4,354,628 and 4,665,916. More particularly, U.S. Pat. No. 4,354,628 discloses a surgical stapler apparatus for forming an array of surgical staples in body tissue including an anvil member against which the staples are crimped, and a staple holder pivotally mounted adjacent one end of the anvil member.

U.S. Pat. No. 4,665,916 discloses a surgical stapling apparatus comprising an anvil assembly against which fasteners are formed and a fastener holder pivotally mounted adjacent one end of the anvil assembly, a spacer member at the other end so constructed to displace tissue that would otherwise obstruct the spacer member from properly positioning the fastener holder relative to the anvil assembly to insure proper fastener formation, and a knife assembly to cut the tissue between the rows of formed fasteners.

Surgeons use such devices by selecting, or targeting the body tissue to be fastened, positioning the stapler mechanism so that the target tissue is between the anvil assembly and the fastener holder, then actuating the fastener holder and drive mechanism. In some surgical applications, though, it is possible to have extraneous untargeted tissue enter the gap between the anvil assembly and the fastener holder when the surgeon is positioning the mechanism. If the extraneous tissue is covered by the target tissue the surgeon may inadvertently activate the stapler mechanism and damage the extraneous surrounding tissue. This problem may occur, for example, in caesarean section procedure when fetal tissue may inadvertently enter the stapler mechanism as the surgeon is carrying out the procedure.

Clearly, therefore, there is a need to provide a surgical stapler whereby the extraneous tissue is protected from the operation of the stapler.

SUMMARY OF THE INVENTION

Accordingly, it is one object of the present invention to provide a surgical stapling apparatus.

It is another object of the present invention to provide a surgical stapling apparatus to fasten body tissue.

It is another object of the present invention to provide a surgical stapling apparatus to simultaneously cut body tissue and apply a plurality of surgical fasteners to body tissue.

It is another object of the present invention to provide a surgical stapling apparatus which isolates the tissue to be joined.

It is yet another object of the present invention to provide a surgical stapling apparatus which shields surrounding tissue from the operation of the stapler.

These and other objects are accomplished herein in an improved surgical stapler mechanism for substantially simultaneously applying a plurality of surgical fasteners to body tissue comprising a handle, a gripping lever, a frame with a U-shaped distal portion, an anvil assembly mounted at the distal leg of the U-shaped distal portion, a fastener holder pivotally connected to the anvil assembly adjacent one end of the anvil assembly thereby defining a gap between them and containing a plurality of surgical fasteners and optionally including a knife means for cutting body tissue, the stapler mechanism further including a fastener driving means for substantially driving all of the fasteners from the fastener holder, and means for actuating the fastener holder, the improvement comprising:

shield means mounted on the sides of the anvil assembly for preventing extraneous body tissue from being operated upon by the surgical stapler, said shield means having a wedge means for separating extraneous tissue from the body tissue to be fastened and deflecting means for deflecting extraneous tissue from entering the gap between the anvil assembly and fastener holder.

Further features of the invention, its nature and various objects will be more apparent from the accompanying drawings and the following detailed description of the invention.

BRIEF DESCRIPTION OF THE DRAWINGS

FIG. 1 illustrates a surgical stapler with tissue shield;

FIG. 2 illustrates a detailed view of the anvil assembly with the shield member, in perspective;

FIGS. 3A, 3B and 3C illustrate in perspective view the anvil assembly, anvil, and shield respectively;

FIGS. 4A and 4B illustrate the operation of the shield before and after closure of the stapling apparatus, respectively; and, FIG. 5 illustrates an exploded view of the fastener holder.

DETAILED DESCRIPTION OF THE INVENTION

Although the principles of the invention are applicable to other similar types of surgical stapler apparatus, the invention will be understood clearly from an explanation of its application to the surgical stapler apparatus of the type mentioned above. The invention is applicable also to both permanent and disposable apparatus. Accordingly, although the invention will be illustrated in a disposable embodiment, it could equally be applicable to a disposable cartridge comprising a fastener holder and an anvil assembly mounted in a permanent instrument.

The surgical stapler apparatus of this invention may be of the type similar to those shown in U.S. Pat. Nos. 4,354,628 and 4,665,916. The disclosures of these patents are incorporated by reference herein.

As shown in FIG. 1 herein, instrument 100 includes handle 102 adjacent the proximal end of the instrument, a longitudinal connecting structure 104 substantially perpendicular to handle 102, and an open U-shaped support structure 106 at the distal end of connecting structure 104; a means such as actuating lever 124 for positioning the fastener holder 118, a means such as gripping level 116 for driving the fasteners, and an anvil assembly support housing 120. Said anvil assembly support housing 120 is riveted to the distal leg 110 of the U-shaped distal support 106, and retains and supports anvil assembly 136 which snaps into said anvil assembly support housing 120. The anvil assembly 136 is the holder for the retainer portions 515 (see FIG. 5) of the two part fasteners. The improvement comprises the shield member 130 which is attached to the anvil assembly 136. The shield 130 automatically pushes aside extraneous surrounding tissue as the surgeon positions the stapler for the joining operation, and it further adjusts itself to regulate the gap distance between the fastener holder 118 and anvil assembly 136.

FIG. 5 shows a detailed exploded view of the interior of the fastener holder 118, which contains fasteners 501, fastener pushers 502, pusher holder 503 with elongated slots 504 for fasteners, knife blade 505, housing 511, spacer 506, alignment pin 128 with spring 507, and base portion 512. As can be seen from FIG. 5, fastener holder 118 is aligned with anvil assembly support housing 120 to which it is pivotably connected. This alignment is aided by alignment pin 128, which pierces the target tissue and is received into depression 303 (see FIG. 3A) in the anvil assembly support housing 120. Retainers 515 are held in the anvil assembly 136 and are released upon engagement with fasteners 501 when the surgical stapler 100 is actuated. Spring 509, biases the fastener holder toward an open position.

Referring again to FIG. 1, shield 130 is a flexible and resilient two legged U-shaped member adapted to fit around the anvil assembly 136. The exterior surface of the end opposite the prongs is rounded and shaped so as to facilitate the separation of tissue with a scooping motion.

The surgical stapler 100 is operated by positioning it such that body tissue to be joined is in the gap between the fastener holder 118, and the anvil assembly support housing 120, to which the holder 118 is pivotally mounted at the base 112 of the U-shaped distal support 106. The anvil assembly support housing 120 is mounted on the distal leg 110 of the distal support 106. The fastener holder is mounted within the proximal leg 108 of the distal support 106.

When the stapler 100 is properly positioned with respect to the tissue the actuator lever 124 is rotated clockwise, thereby pivoting the fastener holder 118 so that it is aligned against the anvil assembly support housing 120. Alignment pin 128 and arch 126 guide the fastener holder 118 into alignment.

The fastener holder 118 is actuated by rotating the gripping lever 116 counterclockwise to operate the drive assembly for driving the fasteners and optionally a knife, into the tissue. Safety latch 114 is normally in a raised position wherein it engages notches 121 to prevent the gripping lever 116 from being rotated. To operate the stapler safety latch 114 is rotated downward to the position as shown in FIG. 1.

As can be seen more clearly in FIG. 2 and FIGS. 3A, 3B and 3C, anvil assembly 136 is seated in anvil assembly support housing 120. Depression 303 in the anvil assembly support housing 120, is for receiving alignment pin 128 when the stapler mechanism is actuated. Shield 130 is a U-shaped member with two leg extensions 302A, 302B and a rounded end 306 which acts as a wedge. The inner surfaces of the two legs each have parallely extending elongated detents 304A, 304B, which are mounted into notches 310A, 310B in the sides of the anvil assembly and adhesively fixed thereto.

The shield 130 is positioned such that the rounded end 306 is oriented towards the open end of the U-shaped distal support structure 106, and it extends beyond the anvil assembly support housing 120.

The width of legs 302A, 302B varies from the fixed end at detents 304A and 304B where the legs 302A, 302B are no wider than the sides of the anvil assembly 136 to which they are attached, to the rounded end 306 where legs 302A, 302B are wider than the sides of the anvil assembly 136, thereby extending beyond the surface of the anvil assembly 136 and closing off entry into the gap space between the anvil assembly 136 and the fastener holder 118. Therefore, legs 302A, 302B are deflecting means for deflecting extraneous tissue from entering the gap space between the anvil assembly 136 and fastener holder 118 and protect said extraneous tissue from inadvertently being operated upon by the stapler.

Shield 130 is a single piece scoop-like construction molded from a plastic of relatively high mechanical strength, such as polycarbonate resin. It must be both flexible and resilient. Indentations 308A and 308B on the edges of the legs distal to the stapler facilitate the flexing of the high strength polymer to a degree sufficient for the scoop to perform its function. The resiliency of the polymer biases the shield back to its unflexed position.

FIGS. 4A and 4B illustrate the functioning of the invention. In FIG. 4A the distal end of the surgical stapler is being brought into position to join body tissue 402. Extraneous tissue 404 underneath tissue 402 would be unseen by the surgeon. But as the legs of the support structure are brought around the tissue, as can be seen in FIG. 4B, the shield member 130 wedges aside the extraneous tissue 404. The rounded end 306 of the shield 130 has a tip 406 with an angle of less than 90° in a direction transverse to the curvature of the end of the shield so as to facilitate the wedge action of the shield.

The shield 130 is free to flex pivotably between a first proximal position and a second distal position in response to pressure exerted upon it by body tissue 402 as the surgeon positions stapler 100 for operation. When targeted tissue 402 enters the gap between the anvil assembly 136 and the fastener holder 118, the shield 130 bends in a direction distal to that of the stapler in response to the pressure exerted upon it. Nevertheless, its resiliency biases it back in a proximal direction towards its unflexed position. The proximal edge of shield 130 contacts the tissue 402 and creates a seal which closes off space whereby extraneous tissue 404 would otherwise find entry into the gap. Therefore, extraneous tissue is deflected and protected from the operation of the stapler.

While the above description contains many specifics, these specifics should not be construed as limitations on the scope of the invention, but merely as exemplifications of preferred embodiments thereof. Those skilled in the art will envision many other possible variations which are within its scope. For example, skilled artisans will readily be able to change the dimensions or use different materials of construction. Therefore, although the invention has been described with reference to certain preferred embodiments, it will be appreciated that other stapler constructions maybe devised, which are nevertheless within the scope and spirit of the invention as defined by the claims appended hereto.

What is claimed is:

1. In an improved surgical stapler for substantially simultaneously applying a plurality of surgical fasteners to body tissue comprising a handle, a gripping lever, a frame with a U-shaped distal portion, an anvil assembly mounted at the distal leg of the U-shaped distal portion, a fastener holder pivotally connected to the anvil assembly adjacent one end of the anvil assembly thereby defining a gap between them and containing a plurality of surgical fasteners and optionally including a knife means for cutting body tissue, the stapler mechanism further including a fastener driving means for substantially simultaneously driving all of the fasteners from the fastener holder, and means for actuating the fastener holder, the improvement comprising:
    shield means mounted on the sides of the anvil assembly for preventing extraneous body tissue from being operated upon the surgical stapler, said shield means having a wedge means for separating extraneous tissue from the body tissue to be fastened and having deflecting means for deflecting the extraneous tissue from entering the gap between the anvil assembly and the fastener holder.

2. The surgical stapler of claim 1 wherein said shield means is a substantially U-shaped member having a rounded end and two legs,
    said two legs providing deflecting means for deflecting extraneous tissue from entering the gap between the anvil assembly and the fastener holder,
    the inside surfaces of said legs being fixed at one end to the sides of the anvil assembly, and the rounded end of the shield means extending beyond the anvil assembly.

3. The surgical stapler of claim 2 wherein the rounded end of said shield means has a tip angled at less than 90° in a direction transverse to that of the curvature of the end, said tip providing wedge means for separating extraneous tissue from the body tissue to be fastened.

4. The surgical stapler of claim 1 wherein the shield means is flexibly pivotable in response to pressure between a first proximal position and a second distal position.

5. The surgical stapler of claim 2 wherein the width of the shield legs near the rounded end is greater than the width of the shield legs near their respective fixed ends, and the shield legs close off entry into the gap between the anvil assembly and fastener holder 6. The surgical stapler of claim 4 wherein the shield means is resiliently biased to its proximal position.

7. The surgical stapler of claim 1 wherein the shield legs each have an indentation on the edge of the legs distal to the stapler.

8. The surgical stapler of claim 1 wherein the shield means is made of resilient material.

9. The surgical stapler of claim 8 wherein the resilient material is a polymeric material.

10. The surgical stapler of claim 9 wherein the polymeric material is a polycarbonate.

11. In an improved surgical stapler for substantially simultaneously applying a plurality of surgical fasteners to body tissue comprising a handle, a gripping lever, a frame with a U-shaped distal portion, an anvil assembly mounted at the distal leg of the U-shaped distal portion a fastener holder pivotally connected to the anvil assembly adjacent one end of the anvil assembly thereby defining a gap between them and containing a plurality of surgical fasteners and including a knife means for cutting body tissue, the stapler mechanism further including a fastener driving means for substantially simultaneously driving all of the fasteners from the fastener holder, and means for actuating the fastener holder, the improvement comprising:
    shield means mounted on the sides of the anvil assembly for preventing extraneous body tissue from being operated upon the surgical stapler, said shield means having a wedge means for separating extraneous tissue from the body tissue to be fastened and having deflecting means for deflecting the extraneous tissue from entering the gap between the anvil assembly and the fastener holder.

12. The surgical stapler of claim 11 wherein said shield means is a substantially U-shaped member having a rounded end and two legs,
    said two legs providing deflecting means for deflecting extraneous tissue from entering the gap between the anvil assembly and the fastener holder,
    the inside surfaces of said legs being fixed at one end to the sides of the anvil assembly, and the rounded end of the shield means extending beyond the anvil assembly.

13. The surgical stapler of claim 12 wherein the rounded end of said shield means has a tip angled at less than 90° in a direction transverse to that of the curvature of the end, said tip providing wedge means for separating extraneous tissue from the body tissue to be fastened.

14. The surgical stapler of claim 11 wherein the shield means is flexibly pivotable in response to pressure between a first proximal position and a second distal position.

15. The surgical stapler of claim 12 wherein the width of the shield legs near the rounded end is greater than the width of the shield legs near their respective fixed ends, and the shield legs close off entry into the gap between the anvil assembly and fastener holder 16. The surgical stapler of claim 14 wherein the shield means is resiliently biased to its proximal position.

17. The surgical stapler of claim 12 wherein the shield legs each have an indentation on the edge of the legs distal to the stapler.

18. The surgical stapler of claim 11 wherein the shield is made of resilient material.

19. The surgical stapler of claim 18 wherein the resilient materials is a polymeric material.

20. The surgical stapler of claim 19 wherein the resilient polymeric material is a polycarbonate.

* * * * *